(12) United States Patent
Valenta et al.

(10) Patent No.: US 7,108,858 B2
(45) Date of Patent: Sep. 19, 2006

(54) NON-ANAPHYLACTIC FORMS OF ALLERGENS AND THEIR USE

(75) Inventors: Rudolf Valenta, Theresienfeld (AT); Susanne Vrtala, Vienna (AT); Luca Vangelista, Heidelberg (DE); Hans-Georg Eichler, Vienna (AT); Wolfgang R. Sperr, Vienna (AT); Peter Valent, Vienna (AT); Christof Ebner, Vienna (AT); Dietrich Kraft, Vienna (AT); Hans Grönlund, Lidingö (SE)

(73) Assignee: Pharmacia Diagnostics AB, Uppsala (SE)

( * ) Notice: Subject to any disclaimer, the term of this patent is extended or adjusted under 35 U.S.C. 154(b) by 0 days.

(21) Appl. No.: 09/897,042

(22) Filed: Jul. 3, 2001

(65) Prior Publication Data

US 2002/0018779 A1    Feb. 14, 2002

Related U.S. Application Data

(63) Continuation of application No. 08/998,549, filed on Dec. 24, 1997, now abandoned.

(30) Foreign Application Priority Data

Sep. 30, 1997  (SE) .................................... 9703531

(51) Int. Cl.
  *A61K 39/395*  (2006.01)
(52) U.S. Cl. ................... 424/275.1; 530/370; 530/868; 514/327
(58) Field of Classification Search ............ 424/275.1; 530/370, 868; 514/327
  See application file for complete search history.

(56) References Cited

U.S. PATENT DOCUMENTS

| 4,269,764 | A | * | 5/1981 | Patterson et al. |  |
|---|---|---|---|---|---|
| 4,629,783 | A | * | 12/1986 | Cosand |  |
| 5,449,669 | A |  | 9/1995 | Metcalfe et al. |  |
| 6,025,162 | A | * | 2/2000 | Rogers et al. ............. 435/69.3 |  |
| 6,126,939 | A | * | 10/2000 | Eisenbach-Schwartz et al. |  |

FOREIGN PATENT DOCUMENTS

| SE | 9534578 | 12/1995 |
| WO | 9211029 A1 | 7/1992 |
| WO | WO 92/11029 | 7/1992 |
| WO | 9410194 A2 | 5/1994 |
| WO | WO 94/10194 | 5/1994 |
| WO | WO 95/34578 | 12/1995 |
| WO | 9603106 A2 | 2/1996 |
| WO | WO 96/03106 | 2/1996 |
| WO | 9724139 A1 | 7/1997 |
| WO | WO 97/24139 | 7/1997 |

OTHER PUBLICATIONS

Mikayama et al. (PNAS, 1993. 90: 10056-10060).*
Vrtala et al. (J. Allergy Clin Immunology Nov. 1996; 98 (5Pt1): 913-921).*
Rogers et al. (Molecular Immunology, 1994; 31(13): 955-966).*
Vrtala et al. (J. Clin. Invest. Apr. 1997; 99(7):1674-1681).*
Ebner et al. (J Immunology Feb. 1993; 150: 1047-1054).*
Ferreira et al., J. Exp. Med. vol. 183, 1996, pp. 599-609.*
Vrtala et al., J. Clin. Invest., vol. 99, No. 7, pp. 1673-1681 (Apr. 1997).
Tamborini et al., Eur. J. Biochem, Biochemical and immunological characterization of recombinant allergen Lo1 p Dialog Information Service, File 154, MEDLINE, Dialog accession No. 08362396, Medline accession No. 9805571 (1997) (Abstract).
Zhang et al., Immunology, Multiple B-and T-cell epitopes on a major allergen of Kentucky Bluegrass pollen, Dialog Information Service, file 154, MEDLINE, Dialog accession No. 08635889, Medline accession No. 96245983 (1996) (Abstract).
Vrtala et al., J. Allergy Clin. Immunol., vol. 98: pp. 713-921 (1996).
Ebner et al., J. of Immunology, vol. 150: pp. 1047-1054 (1993).
L. Zhang et al., Immunology, 87(2), p. 283-290 (Feb. 1996) (abstract only).
S. Vrtala et al., J. Clin. Invest., 99(7) pp. 1673-1681 (Apr. 1997).
Ebner et al., Journal of Immunology, 150(3) pp. 1047-1054 (Feb. 1, 1993).
E. Tamborini et al., Eur. J. Biochem. 249(3) pp. 886-894 (Nov. 1, 1997) (abstract only).
S. Vrtala et al., J. Allergy Clin. Immunol., 98(5):1, pp. 913-921 (Nov. 1996).

* cited by examiner

*Primary Examiner*—Patrick J. Nolan
(74) *Attorney, Agent, or Firm*—Dinsmore & Shohl LLP

(57) ABSTRACT

The present invention is drawn to an immunogen derived from a protein allergen, which is a) a non-anaphylactic immunogenic recombinant fragment of the protein allergen which contains an IgG epitope partly but not wholly overlapping an IgE epitope of the protein allergen; b) a polymeric form of the fragment, in which the fragment constitutes the monomeric units; or c) a non-anaphylactic recombinant polymeric form of the protein allergen having 2–10 monomeric units, in which the protein allergen constitutes the monomeric units. The present invention is further drawn to the use of the immunogen for in vitro diagnoses of type I allergy and hyposensitization.

8 Claims, 9 Drawing Sheets

CONSTRUCTION OF THE BET V 1 POLYMERS

Bet v 1-Dimer

ATG......AAC TTG GTA CCG ATG.....ACC TAA
Met......Asn Leu Val Pro Met.....Asn End
  Bet v 1               Bet v 1

[Plasmid map: pET-17b with 2 x Bet v 1, sites Nde I, Kpn I, Xho I]

Bet v 1-Trimer

ATG......AAC TTG GTA CCG ATG.....AAC CCA CTA GTA ATG.....AAC
Met......Asn Leu Val Pro Met.....Asn Pro Leu Val Met.....Asn
  Bet v 1            Bet v 1           Bet v 1

GGA TTC TGC AGA TAT CCA TCA CAC TGG CGG CCG CTC GAG CAG ATC
Glu Phe Cys Arg Tyr Pro Ser His Trp Arg Pro Leu Glu Gln Ile

CGG CTG CTA ACA AAG CCC GAA AGG AGG CTG AGT TGG CTG CTG CCA
Arg Leu Leu Thr Lys Pro Glu Arg Lys Leu Ser Trp Leu Leu Pro

CCG CTG AGC AAT AAC TAG
Pro Leu Ser Asn Asn End

[Plasmid map: pET-17b with 3 x Bet v 1, sites Nde I, Kpn I, Spe I, Eco R I]

FIG. 1A

Bet v 1-Tetramer

ATG......AAC TTG GTA CCG ATG.....AAC CCA CTA GTA ATG.....AAC
Met.....Asn Leu Val Pro Met.....Asn Pro Leu Val Met     Asn
   Bet v 1                  Bet v 1                 Bet v 1

GAA TTC ATG.....AAC TAA
Glu Phe Met.....Asn End
         Bet v 1

NON-ANAPHYLACTIC FORMS OF ALLERGENS AND THEIR USE

This application is a continuation of application Ser. No. 08/998,549, filed on Dec. 24, 1997, the entire contents of which are hereby incorporated by reference and for which priority is claimed under 35 U.S.C. § 120; and this application claims priority of application Ser. No. 9703531-5 filed in Sweden on Sep. 30, 1997 under 35 U.S.C. § 119.

TECHNICAL FIELD AND BACKGROUND

The invention concerns non-anaphylactic forms of protein allergens and the use of the forms for hyposensitization and for determining antibodies (IgA, IgD, IgE, IgG, IgM) directed against the allergen, for instance in the context of diagnosing in vitro type I allergy (IgE mediated allergy). The invention also concerns a method for hyposensitization of a mammalian individual, typically a human individual, suffering from type I allergy against a protein allergen.

The invention primarily concerns treating and diagnosing humans.

By a protein allergen is meant any protein/polypeptide causing a type I mediated allergic reaction. Thus the term encompasses any naturally occuring protein allergen including the smallest fragments thereof that will cause a type I allergic reaction in a mammal, most importantly humans.

In April 1997, the present inventors have published an article dealing with non-anaphylactic fragments of the Bet v 1 allergen. See Vrtala et al., "Conversion of the major birch pollen allergen, Bet v 1, into two non-anaphylactic T cell epitope containing fragments", J. Clin. Invest. 99(7) April 1997) 1673–1681.

Type I allergy represents a major health problem in industrialised countries where more than 20% of the population suffer from Type I allergic reactions (allergic rhinitis, conjunctivitis, allergic asthma and anaphylactic shock) (Kaplan (ed) Allergy. Churchill Livingstone, New York (1985)). Environmental proteins from pollen, mites and animal dander belong to the major components which induce release of biological mediators (e.g. histamine) by crosslinking effector cell (mast cell, basophil) bound specific IgE antibodies. The production of specific IgE from B-cells is stimulated by allergen specific T-helper cells which in their majority belong to the TH2 type (Romagnani, Immunol Today 13 (1992) 379–381). Therapy of Type I allergic diseases is currently performed by pharmacological treatment and by specific immunotherapy. Specific immunotherapy has been established already early in this century (Noon, Lancet 1 (1911) 1572–1573) and involves the systemic application of increasing doses of allergens for extended periods. Although specific immunotherapy is recognized as effective treatment, the occurrence of anaphylactic side effects represents one of the major disadvantages of this therapy. To reduce anaphylactic reactions the use of T-cell epitopes has recently been proposed for allergen specific immunotherapy (Briner et al., Proc. Natl. Acad. Sci. USA 90 (1993) 7608–7612, and Norman, Curr. Opin. Immunol 5 (1993) 986–973). Allergens harbour a great variety of different T-cell epitopes (Ebner et al., J. Immunol 150 (1993) 1047–1054; Joost-van-Neerven et al., J. Immunol. 151 (1993) 2326–2335; and Schenk et al., J. Allergy Clin. Immunol. 96 (1995) 986–996) which may overlap with continuous IgE-epitopes. To prevent crosslinking of effector cell (mast cell, basophil) bound IgE and mediator release, T-cell epitopes and IgE epitopes need to be dissected. Following the concept of converting a major allergen into a T-cell vaccine we have selected Bet v 1 (Breiteneder et al., EMBO J. 8 (1989) 1935–1938), the major birch pollen allergen as a model. Bet v1 was selected because epitope analysis indicated that it forms conformational IgE epitopes (Visco et al., J. Immunol. 157 (1996) 956–962; and Laffer et al., J. Immunol. 157 (1996) 4953–4962). In addition Bet v1 represents one of the most common allergens which is recognized by 95% of tree pollen and food allergic individuals and almost 60% of them are sensitisized exclusively against Bet v1 (Jarolim et al., Allergy 44 (1989) 385–394). The cDNA coding for Bet v1 has recently been isolated (Breitenederet al., EMBO J. 8 (1989) 1935–1938) and recombinant Bet v1 was expressed in *Escherichia coli* (Valenta et al., J. Allergy Clin. Immunol. 88 (1991) 889–894; and Ferreira et al., J. Biol. Chem. 268 (1993) 19574–19580). Recombinant Bet v1 has been shown to possess similar IgE-binding capacity as natural Bet v1 and shares IgE as well as T-cell epitopes with Bet v1 homologous proteins present in pollen from various trees and plant derived foods (Ebner et al., J. Allergy Clin Immunol. 95 (1995) 962–969; Ebner et al., J. Immunol 150 (1993) 1047–1054; and Schenk et al., Eur. J. Biochem. 224 (1994) 717–724). The biological activity of the recombinant Bet v1 has been demonstrated by histamine release experiments and by skin prick testing of allergic patients (Valenta et al., J. Allergy Clin. Immunol. 91 (1993) 88–97; Pauli et al., J. Allergy Clin. Immunol. 98 (1996) 1100–1109; and Menz et al., Clin. Exp. Allergy 26 (1995) 50–60).

BRIEF SUMMARY OF THE INVENTION

FIGS. 1(A) and 1(B) depict the construction of the Bet V 1 polymers.

FIG. 2 shows a coomassie stained SDS-PAGE gel with purified recombinant Bet v 1-monomer and Bet v 1-polymers.

FIGS. 3(A)–3(C) show the IgE reactivity of birch-pollen allergic patients with nitro-cellulose-blotted purified recombinant Bet v 1-monomer, dimer and trimer.

FIGS. 4(A)–4(D) show the determination of IgE reactivity of sera from birch pollen allergic patients with Bet v 1-monomer and polymers by ELISA.

FIGS. 5(A)–5(D) show the inhibition of IgE-binding to recombinant Bet v 1-monomer using Bet 1-polymers.

Figures 8A, 8B:
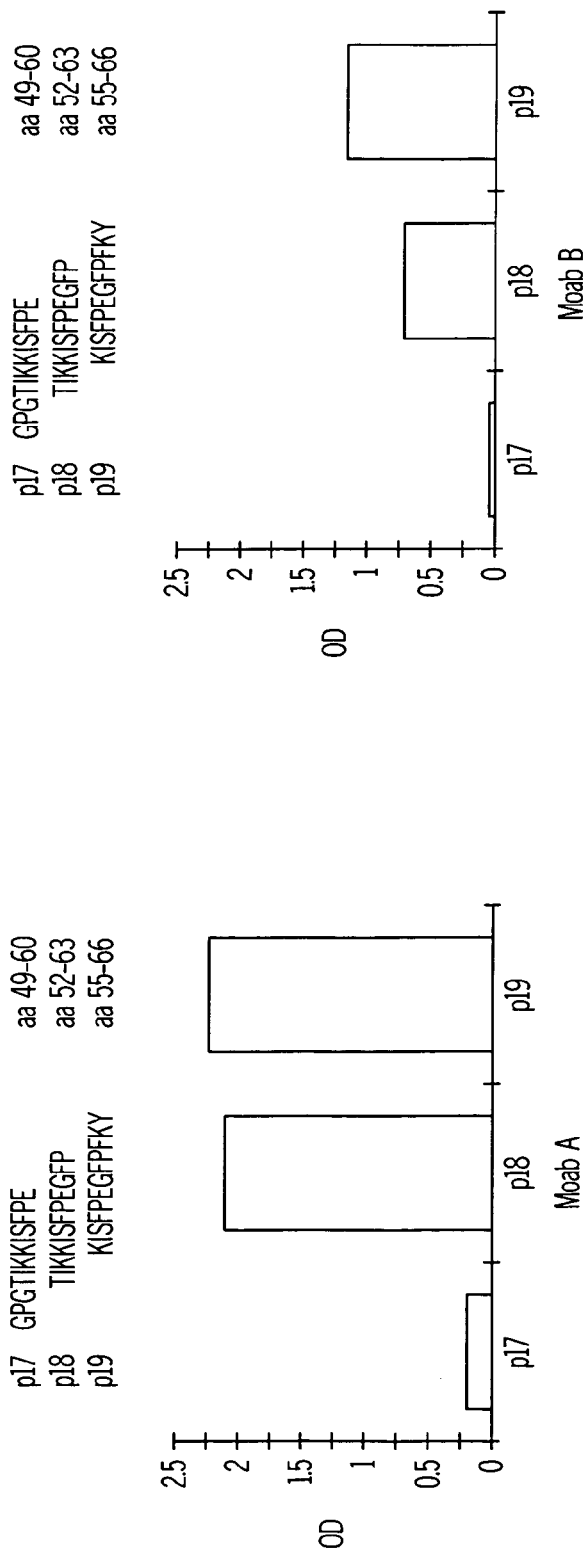

FIGS. 8(A)–8(B) show binding of monoclonal anti-Bet v 1-antibodies to Bet v 1-derived peptides.

THE INVENTION

The first aspect of the invention is an immunogen derived from a protein allergen. It has a strongly reduced anaphylactic ability compared to the protein allergen from which it derives and will therefore in the context of the present invention be called non-anaphylactic. The immunogen is characterized in that it comprises:

a. a non-anaphylactic immunogenic recombinant fragment of the protein allergen, said fragment containing an IgG epitope partly but not wholly overlapping an IgE epitope of the protein allergen, said IgE epitope having been broken up by fragment formation;

b. a polymeric form of said fragment, in which form the fragment constitutes the monomeric units;

c. a recombinant polymeric form of said protein allergen in which the protein allergen constitutes the monomeric units.

By the term "a broken up IgE epitope" is meant that the fragment formation has resulted in a fragment that only contains a part of the correponding IgE epitope present in the starting protein allergen. The epitopes in question may be either conformational or linear, with particular emphasis for the IgE epitope being conformational in case of a fragment according to items (a) and (b). Compare Bet v 1 fragments aa 1–74 and 75–160 as described in the experimental part and by Vratala t al., J. Clin. Invest. 99(7) April 1997) 1673–1681.

By polymeric forms means that the immunogen typically comprises 2–10 of the monomeric units defined in (b) and (c). At the priority date results had been obtained with polymeric forms containing 2, 3 and 4 monomeric units.

The various forms a–c may be produced by recombinant techniques to directly give a fragment according to (a), or a polymeric form according to (b) or (c). For (b) the polymeric form may also be accomplished by covalently linking two or more identical recombinant fragment molecules to a common carrier molecule. In the final immunogen that is to be used for hyposensitization therapy or in vitro assays, the fragment according to (a) and the polymeric forms according to (b) and (c) may have been linked to a carrier in order to increase the immunogenicity. In case this carrier is a protein and one wants to have a linear immunogen it is possible to produce the immunogen in one step by expression of the corresponding gene construct in the appropriate host cell, such as aa procaryotic (e.g. *E. coli*) or eucaryotic (yeast or a mammalian cell line) cell. See further Scheiner O and Kraft D, Allergy 50 (1995) 384–391; and Valenta R and Kraft D, Current Opinion in Immunology 7 (1995) 751–756.

By the use of recombinant techniques it is easy to introduce oligopeptide linkers between each monomeric unit of the polymeric form of the immunogen according to items (b) and (c). Suitable amino acid residues in the linker may be selected among hydrophobic or hydrophilic or among basic, acid or neutral amino acids. Hydrophobic amino acids are trp, gly, ala, phe, pro, met, val, leu, and ile. Hydrophilic amino acids are for instance gln, ser, gly, glu, pro, his and arg. The length of the oligopeptide linker typically is an integer in the interval 0–30, such as in the interval 0–10, amino acid residues. At the priority date the preferred linker was the tripeptide leu-val-pro.

In the experimental part the invention is illustrated with the birch pollen allergen Bet v 1.

The second aspect of the invention is specific hyposensitization therapy. This therapy may be performed as known in the art for protein allergens and encompasses administering repeatedly to the mammal, typically a human individual, suffering from type I allergy against the protein allergen an immunogen that is capable of raising as IgG immune response against the protein allergen. Administration may be done systemically, for instance by injection, infusion, etc., but also the oral route has been suggested in order to expose the intestinal part of the immune system. The immunogen may be admixed with suitable adjuvants such as aluminium oxide. See further Norman P S, "Current status of immunotherapy for allergies and anaphylactic reactions" Adv. Internal. Medicine 41 (1996)681–713.

A third aspect of the invention is to use the immunogen of the first aspect, in particular according to item (c) as an antigen in an immunoassay for detecting specific antibodies of the IgA, IgD, IgE, IgG or IgM class directed against the protein allergen or protein allergens from which the immunogen derives. Appropriate assays variants involve formation of a ternary immune complex between the immunogen, sample antibody and an antibody directed against the Ig-class of interest. The sample may be any Ig-containing biological fluids, for instance a blood derived sample (serum, plasma, whole blood), CSF, etc.

The invention will be defined in the attached claims that are part of the specification. The invention will now be illustrated by two non-limiting patent examples.

EXPERIMENTAL PART

EXAMPLE 1

Bet v 1 Polymers

Construction of the Bet v 1-polymers

The Bet v 1-cDNA (Breiteneder et al., "The gene coding for the major birch pollen allergen Bet v 1 is highly homologous to a pea resistance response gene", EMBO J. 8 (1989) 1935–1938) was PCR-amplified with the following oligonucleotide primers:

```
Bet v 1-dimer:
For construction of the first Bet v 1-segment:
   5'GAG GAA TTC CAT ATG GGT GTT TTC AAT TAC3'    (SEQ ID NO:1)
       Eco R I Nde I 5'CGG GGT ACC AAG TTG TAG GCA TCG GAG TG3'    (SEQ ID NO:2)
       Kpn I For construction of the second Bet v 1-segment:
  5'CGG GGT ACC GAT GGG TGT TTT CAA TTA C3'      (SEQ ID NO:3)
       Kpn I 5'CCG GAA TTC CCG CTC GAG CTA TTA GTT GTA GGC ATC   (SEQ ID NO:4)
  GGA GTG3'
       Eco R I   Xho I
```

Bet v 1-trimer:

The first Bet v 1-segment: The same primers were used as for construction of the first segment of Bet v 1-dimer.

```
Second Bet v 1-segment:
    SEQ ID NO:5:
    5'CGG GGT ACC GAT GGG TGT TTT CAA TTA C3'
        Kpn I SEQ ID NO:6:
    5'CGG AAT TCA CTA GTG GGT TGT AGG CAT CGG AGT G3'
         Eco R I Spe I Third Bet v 1-segment:
    SEQ ID NO:7:
    5'CCG GAA TTC GGA CTA GTA ATG GGT GTT TTC AAT TAC3'
          Eco R I       Spe I SEQ ID NO:8:   5'CGG AAT TCG TTG TAG GCA TCG GAG TG3'
          Eco R I
```

Protocol for PCR-amplification: Reaction mix (GeneAmp PCR kit, Perkin Elmer, Branchburg, N.J. USA): 44 µl $H_2O_{dd}$, 10×1 10×PCR buffer, 4 µl 5 mM dATP, 4 µl 5 mM dCTP, 4 µl 5 mM dGTP, 4 µl 5 mM dGTP, 4 µl 25 mM $MgCl_2$, 3 µl 10×M primer 1, 3 µl 10×M primer 2, 10 µl 1 ng/µl Bet v 1. 10×PCR-buffer: 100 mM Tris-HCl, pH8.3, and 500 mM KCl. The reaction mixture was heated for 5 minutes at 94° C., afterwards 35 cycles of 1 min at 94° C., 2 min at 40° C., and 3 min at 72° C. were performed. During the first cycle 10 µl of AmpliTaq DNA Polymerase (2.5 U/10 µl) were added.

After PCR-amplification, the PCR-products were digested with the corresponding restriction enzymes. Primers which contained additional Eco R I sites, were digested first with Econ R I to facilitate subcloning. Digested fragments were purified using Nick columns (Pharmacia Biotech Ab, Uppsala, Sweden), and ligated into pET-17b plasmids (Novagen, Madison, USA). The plasmid, containing the first Bet v 1-segment, was further digested with Kpn I/Xho I in the case of Bet v 1-dimer, or with Kpn I/Spe I in the case of Bet v 1-trimer, to obtain vectors, in which the second Bet v 1-segments could be incorporated. In the case of Bet v 1-trimer, this construct was further digested with Spe I/Eco R I and the third Bet v 1-segment was added.

Expression and purification of recombinant Bet v 1-polymers.

Recombinant Bet v 1-dimer and recombinant Bet v 1-trimer were expressed in *E. coli* BL21 (DE3) by induction with 0.5 mM isopropyl beta-thiogalactopyranoside at an OD600 of 0.5–0.8 in liquid culture (LB-medium) for 5 h at 37° C. *E. coli* cells were the harvested by centrfugation and washed to remove the culture medium.

LB-medium: 10g sodium chloride, 10 g peptone, 5 g yeast extract, pH 7.5 with NaOH,autoclaved prior to use.

Purification. Recombinant Bet v 1-polymers were expressed as inclusion bodies and isolated as described (Vrtala et al., "Immunologic characterization of purified recombinant timothy grass pollen (Phleum pratense) allergens (Phl p 1, Phl p 2, Phl p 5)", J. Allergy Clin. Immunol. 97n (1996) 781–786. Inclusion bodies were solubilized with 8M urea, 10 mM Tris, pH 8, 1 mM EDTA, 5 mM beta-mercaptoethanol, diluted with 10 mM Tris, pH 8, to a concentration of 6M urea and centrifuged for 15 min at 10,000 g to remove insoluble material. The supernatant, containing the recombinant protein, was dialyzed to a final concentration of 2M urea. After centrifugation (15 min, 10,000 g), the supernatant was applied to a column packed with DEAE Sepharose (Pharmacia Biotech AB, Uppsala, Sweden), and the protein was eluted with a 0–0.5M NaCl-gradient. Fractions, containing the recombinant protein which was >80% pure, were dialyzed against 6M nurea, 10 mM $NaH_2PO4$, pH 4.8, and rechromatographed on a column packed with SP Sepharose (Pharmacia Biotech AB, Uppsala, Sweden) Fractions, containing recombinant Bet v 1-dimer or recombinant Bet v 1-trimer of >95% purity were dialyzed against 10 mM Tris, pH 7.5 and stored at −20° C. until used.

Results of Studies on Bet v 1 polymers.

Figure 1B:
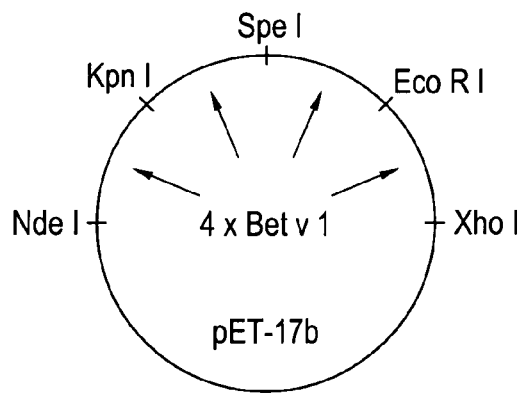

FIG. 1. Construction of the Bet v 1 polymers.

The Bet v 1-cDNA (Breiteneder et al., EMBO J. 8 (1989) 1935–1938) was PCR-amplified with oligonucleotide primers containing different restriction enzyme cleavage sites. The PCR-products were then ligated as indicated in the figure and subcloned into the plasmid pET-17b (Novagen, Madison, USA). Bet v 1-Dimer (SEQ ID NOS: 13 and 14). Bet v 1-Trimer (SEQ ID NOS: 15 and 16) and Bet v 1-Tetramer (SEQ ID NOS: 17 and 18).

Figure 2:
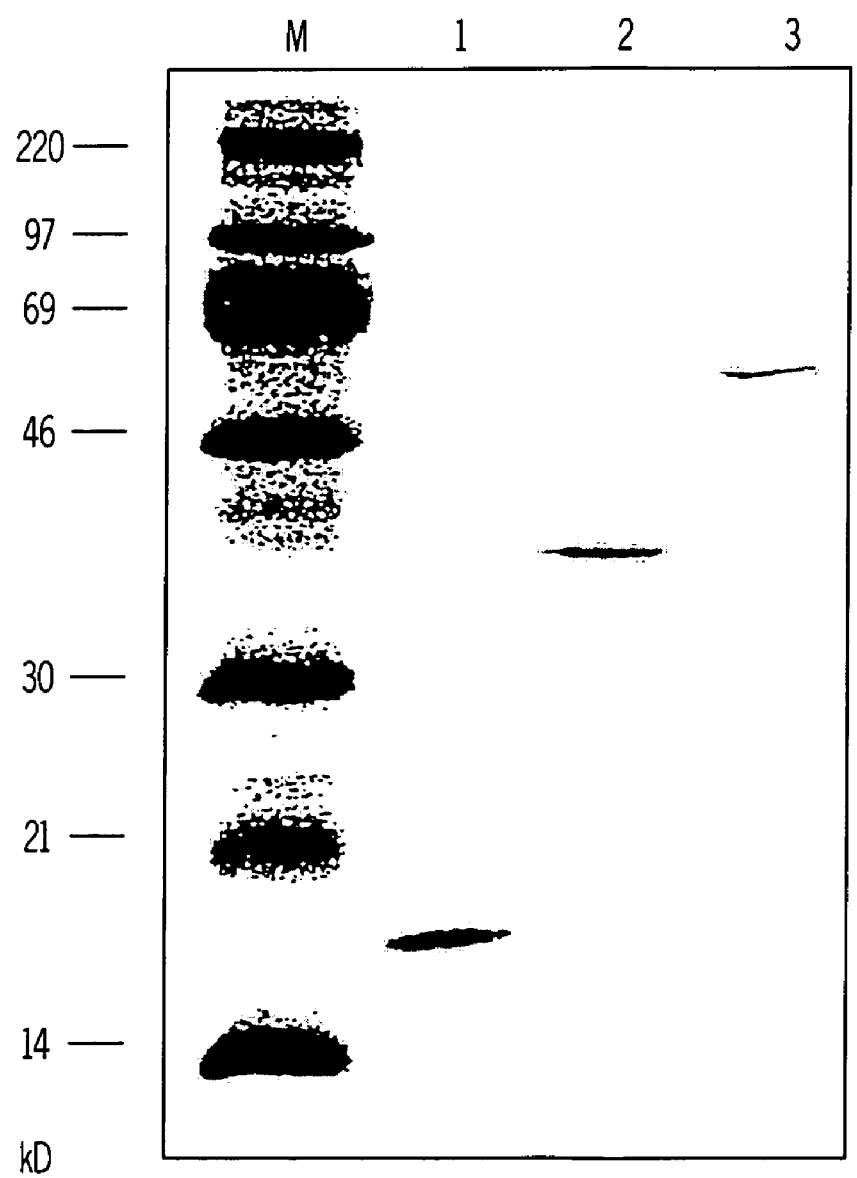

FIG. 2. Coomassie Stained SDS-PAGE gel Showing Purified Recombinant Bet v 1-monomer and Bet v 1-polymers Lane M: Molecular weight marker; lane 1 contains 3 µg purified, recombinant Bet v 1 monomer, lane 2 3 µg purified, recombinant Bet v 1-dimer, lane 3 3 µg purified recombinant Bet v 1-trimer and lane 4 3 µg purified, recombinant Bet v 1-tetramer.

Result: The purified proteins were more than 95% pure. The dissolved proteins were separated from insoluble material by high speed centrifugation prior to loading the samples.

Figure 3A:
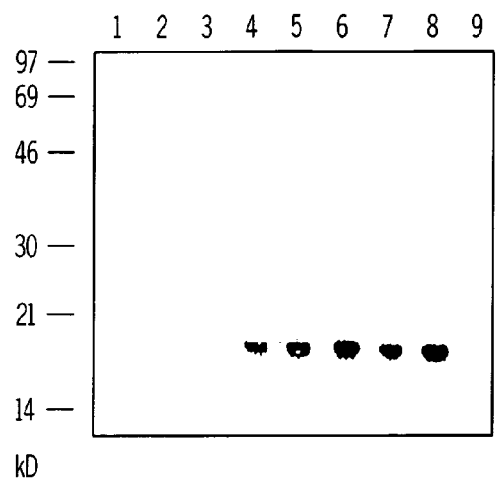
Figure 3B:
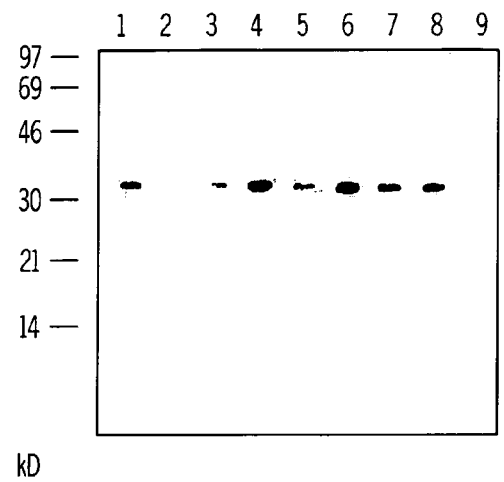
Figure 3C:
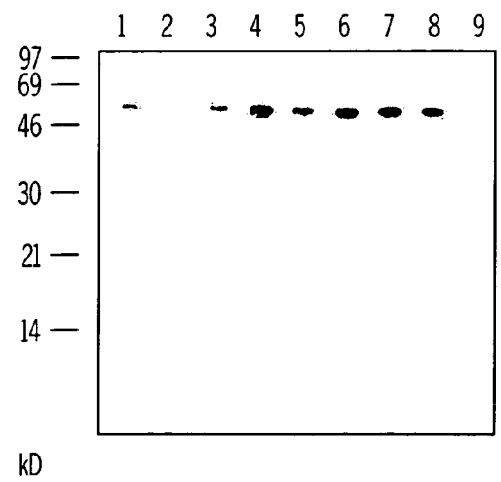
Figure 4A:
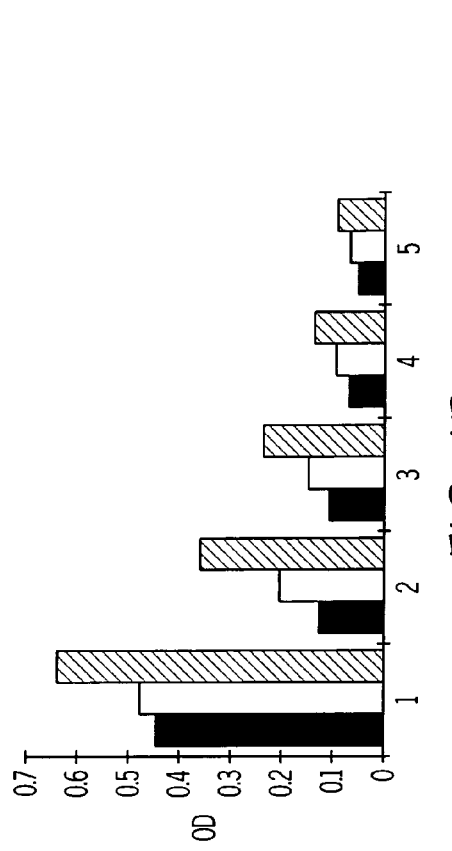
Figure 4B:
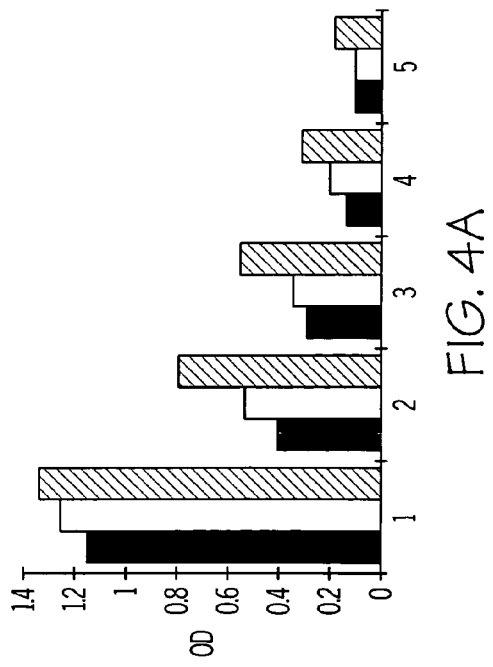
Figure 4C:
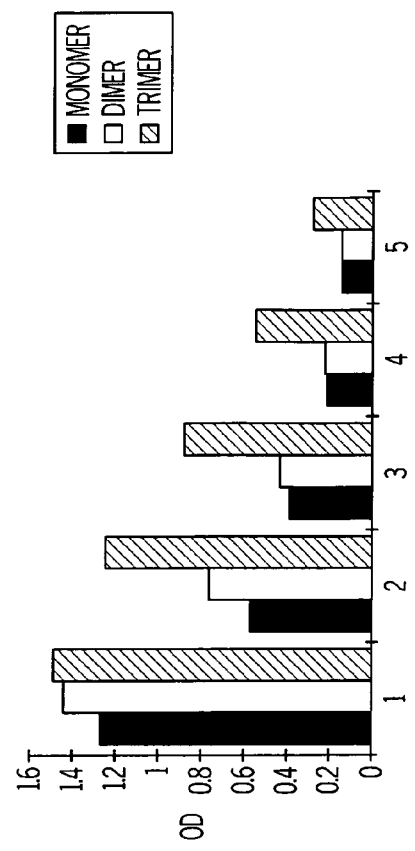
Figure 4D:
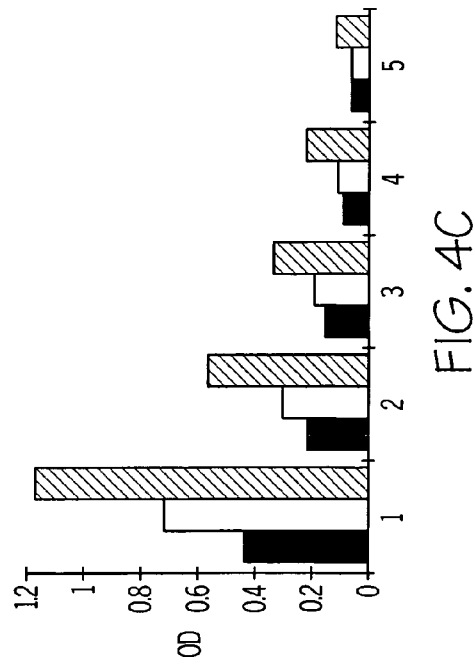
Figure 5A:
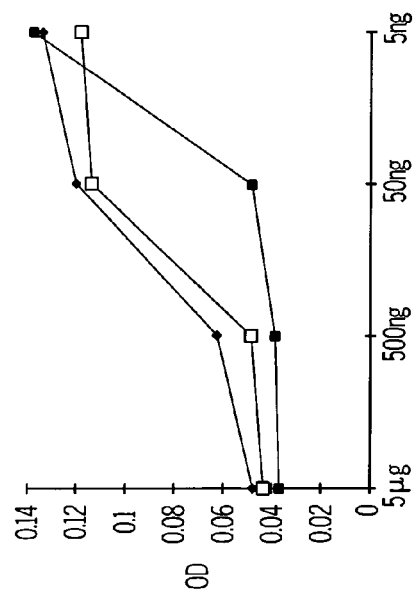
Figure 5B:
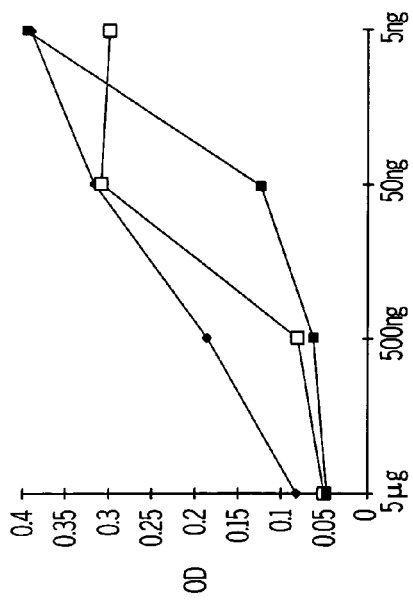
Figure 5C:
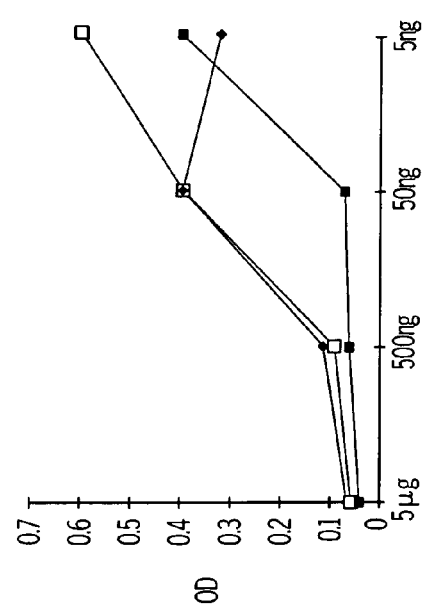
Figure 5D:
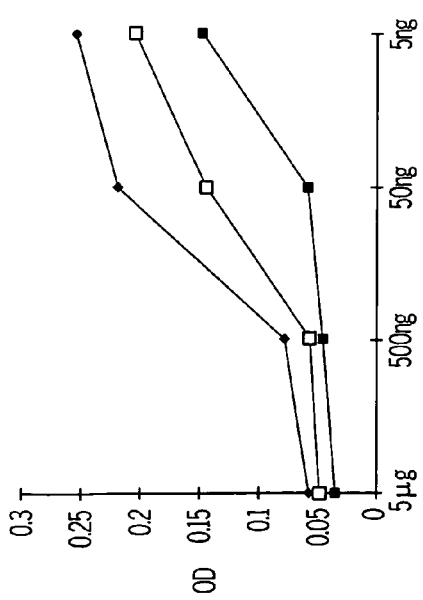

FIG. 3. IgE-reactivity of Birch-pollen Allergic Patients with Nitro-cellulose-blotted Purified Recombinant Bet v1-monomer, Dimer and Trimer.

Purified recombinant Bet v 1-monomer, dimer and trimer were separated by SDS-PAGE and blotted onto nitro-cellulose. Sera from 8 different birch pollen allergic patients (lanes 1–8) and serum from a non-allergic person (lane 9) were used to detect the blotted allergens. Bound IgE was detected with 125I labelled anti-human >IgE antibodies (Pharmacia & Upjohn Diagnostics, Uppsala, Sweden) and visualised by autoradiography.

Result: The IgE-binding capacity of nitrocellulose-blotted Bet v 1-polymers was comparable to Bet v 1-monomer.

FIG. 4: Determination of IgE-reactivity of Sera from Birch Pollen Allergic Patients with Bet v 1-monomer and Polymers by ELISA Sera from 4 birch-pollen allergic patients (A–D) were diluted 1:2 (1), 1:10 (2), 1:20 (3), 1:40 (4) and 1:80 (5) and tested for IgE-reactivity with purified, recombinant Bet v 1-monomer, Bet v 1-dimer and Bet v 1-trimer. The OD-values are displayed on the y-axis.

Result: Serum IgE from allergic patients bound to Bet v 1-polymers in a comparable manner as to Bet v 1-monomer.

FIGS. 5(A) to 5(D). Inhibition of IgE-binding to recombinant Bet v 1-monomer using Bet v 1-polymers.

Sera from 4 birch-pollen allergic patients (A–D) were preincubated with different concentrations (5 µg, 500 ng, 50 ng and 5 ng) of purified, recombinant Bet v 1-monomer, Bet v 1-dimer and Bet v 1-trimer. The preincubated sera were then tested for IgE-reactivity to purified, recombinant Bet v 1-monomer by ELISA. The optical densities are displayed on the y-axis.

Figure 6:
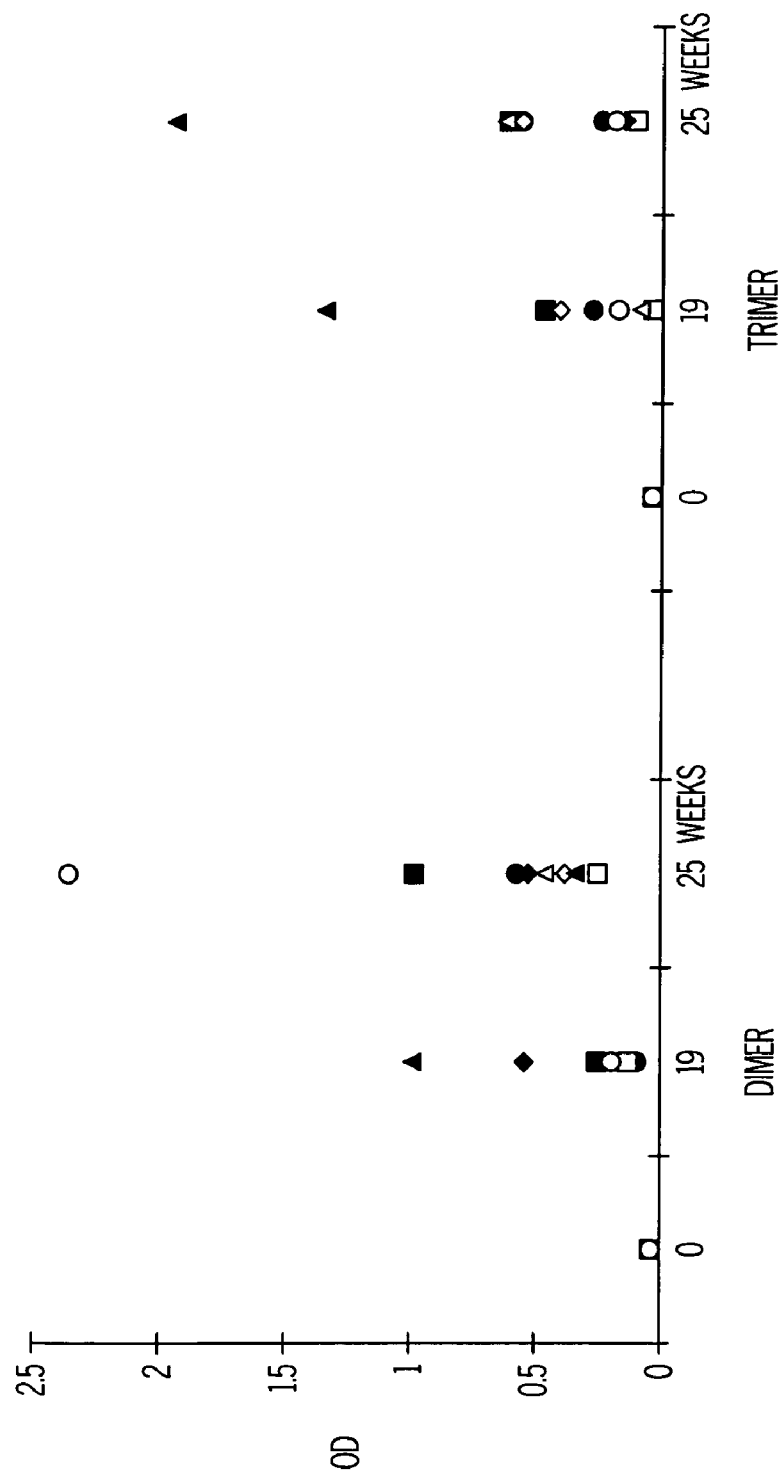
FIG. 6 shows serum $IgG_1$-reactivity of Bet v 1-polymer immunized mice with recombinant Bet v 1.

FIG. 6. Serum $IgG_1$-reactivity of Bet v 1-polymer Immunized Mice with Recombinant Bet v 1

8 Balb/c mice were immunized monthly with 5 µg purified, recombinant Bet v 1-dimer and $Al(OH)_3$ as adjuvant, 8 Balb/c mice were immunized monthly with 5 µg purified, recombinant Bet v 1-trimer-$Al(OH)_3$ and blood samples were taken after each immunization. Serum samples obtained after weeks 19 and 25 of immunization and serum taken before immunization (preimmune serum 0=) were diluted 1:1000 and tested for $IgG_1$-reactivity with purified, recombinant Bet v 1-monomer in an ELISA. The symbols represent the OD-values that corresponds to the IgG1-binding of the 8 different Bet v 1-dimer or Bet v 1-trimer mice.

Result: The Bet v 1-polymers are able to induce high levels of IgG1-antibodies, which crossreact with Bet v 1-monomer.

Figure 7:
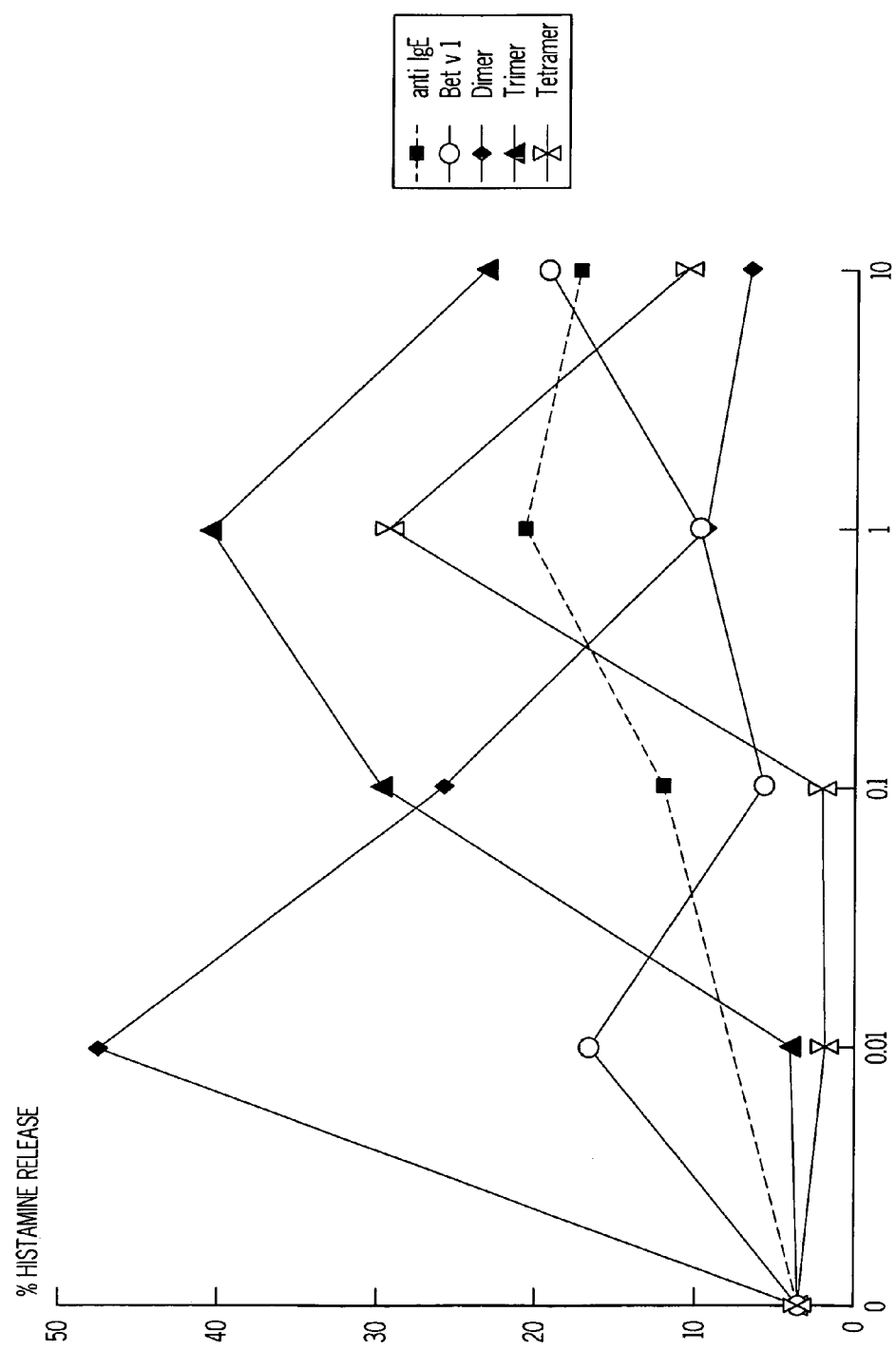
FIG. 7 shows the capacity of recombinant Bet v 1-polymers to induce histamine release.

FIG. 7. Capacity of Recombinant Bet v 1-polymers to Induce Histamine Release

Granulocytes from two different birch pollen allergic patients (a,B9 were incubated with increasing concentrations (0.01 µg/ml, 0.1 µg/ml, 1 µg/ml and 10 µg/ml) of purified, recombinant Bet v 1-monomer, Bet v 1-dimer, Bet v 1-trimer, Bet v 1-tetramer and anti-IgE antibodies as positive control. Histamine release in the cell free supernatant was measured by RIA (Immunotech, Marseille) and is expressed as percentage of total histamine release.

Result: Bet v 1-dimer induced an approximately 2 fold reduced histamine release from patients' basophils compared to Bet v 1-monomer, whereas Bet v 1-trimer and tetramer had an approximately 100 fold reduced capacity to induce histamine release. In the donors tested, Bet v 1-monomer induced maximal histamine release at a concentration of 0.01 µg/ml, Bet v 1-trimer and tetramer at a concentration of 1 µg/ml.

Table 1. Proliferation of Bet v 1 Specific T-cell Clones with Recombinant Bet v 1-polymers The full table is given at the end of the descriptive part. T-cell clones from different pollen allergic donors (column 2 shows the initials of the donors) with specificity for different Bet v 1 epitopes (in column 1 the position of the epitopes are indicated) were incubated with purified, recombinant Bet v 1-monomer (column 4), Bet v 1-dimer (column 5), Bet v 1-trimer (column 6) and Bet v 1-tetramer (column 7). As negative control, clones were tested with medium alone (column 3). Proliferation was determined by $^3H$ Thymidine uptake and is displayed as counts per minute (cpm) (columns 3–7).

Result: Bet v 1-polymers and Bet v 1-monomer induced comparable proliferation of specific T cell clones.

Table 2. Skin Testing with Recombinant Bet v 1-monomer and Polymers

The full table is given at the end of the descriptive part. 6 birch-pollen allergic individuals and 4 non-allergic control individuals were skin prick tested on their forearms with natural birch pollen extract, histamine as positive control and with 10 µg/ml and 100 µg/ml of purified, recombinant Bet v 1-monomer, Bet v 1-dimer and Bet v 1-trimer. The mean wheal diameters (DM) are displayed in the table.

Result: Bet v 1-dimer induced an approximately 10-fold reduced skin reaction in allergic patients compared to Bet v 1-monomer, whereas Bet v 1-trimer induced in some patients no wheal reactions at all, up to a concentration of 100 µg/ml. The wheal reaction increased dose dependently with the protein concentrations. The non-allergic control individuals displayed only skin reactions with histamine but not with the Bet v 1-preparations. Both the histamine release assays and the skin tests indicate, that the Bet v 1-polymers have a greatly (up to 100 fold) reduced anaphylactic activity compared to Bet v 1-monomer. The reduction of anaphylactic potential is proportional to the degree of polymerization.

SUMMARY

Studies on Bet v 1 Polymers

We expressed in pET 17b plasmids (Novagen, Madison, USA) Bet v 1 as dimer, trimer and tetramer. The Bet v 1-polymers were expressed at high levels in *E. coli* BL21 (DE3) (Novagen, Madison, USA) and purified to homogeneity. The Bet v 1-polymers retained their IgE-binding capacity, as was shown by immunoblotting and by ELISA. T-cell clones from birch allergic donors, with specificity for Bet v 1 proliferated upon incubation with all the polymers, indicating that the polymers contain the relevant T-cell epitopes of Bet v 1. Bet v 1-trimer and tetramer had an approximately 100 fold reduced capacity to induce histamine release from patients' basophils and a greatly reduced anaphylactic potential as evaluated by skin testing. Because of the reduction of their anaphylactic activity the Bet v 1-polymers may be considered as safe tools for specific immunotherapy of tree pollen and associated food allergy. allergic patients may be treated with high doses of these derivatives with reduced risk of anaphylactic side effects. The difference of the recombinant polymers to non-anaphylactic T-cell epitope containing allergen derivative is that they contain the IgE-binding sites but have a reduced anaphylactic potential.

EXAMPLE 2

Mapping the Binding Site of Antibodies in Bet v 1

FIG. 8: Two monoclonal anti-Bet v 1-antibodies (moAb A and B) were used together with three synthetic Bet v 1-derived peptides were used in ELISA. The sequences of the three peptides are shown in the lower part of the figure and corresponds to aa 49–60 (SEQ ID NO:19) (p17), aa 52–63 (SEQ ID NO:20) (p18) and aa 55–66 (SEQ ID NO:21) (p19) of Bet v 1. The peptides were tested for binding to the two Bet v Ispecific monoclonals. The OD values are displayed on the y-axis. Both moAbs bind to the peptides p18 and p19, which are mapped to the first half of Bet v 1.

Table 3. The full table is given at the end of the descriptive part. Monoclonal anti-Bet v 1 antibodies (A,B) inhibit binding of human IgE to recombinant Bet v 1. Dot-blotted Bet v 1 was preincubated with MoAb A and B prior to probing with serum IgE from 60 Bet v 1 allergic individuals. Bound IgE was detected with 125I-labelled anti-human IgE antibodies and quantified by gamma-counting. Inhibition of IgE binding was determined as follows:

$$100-(cpm_1/cpm_2)100=\%inhibition$$

$cpm_1$=count per minutes for incubation with moAb $cpm_2$=count per minutes for incubation buffer The % inhibition of IgE-binding compared to preincubation with buffer is displayed in the table.

EXAMPLE 3

Two Non-anaphylactic Recombinant Fragments Bet v 1

See further Vrtala et al., "Conversion of the major birch pollen allergen, Bet v 1, into two non-anaphylactic T cell epitope containing fragments", J. Clin. Invest. 99(7) April 1997) 1673–1681.

Methods

Sera from allergic patients, antibodies, protein extracts and E. coli strains. Sera from birch pollen allergic patients and control individuals were characterized by RAST and testing with recombinant allergens as described (Valenta et al., J. Allergy Clin. Immunol. 88 (1991) 889–894; Valenta etal., Int. Arch. Allergy Immunol. 97 (1992) 287–294). In addition all patients were characterized by case history and skin pricl test. The mouse monoclonal antibody moab 14 with specificity for aa 40–65 of Bet v 1 is described (Lebecque et al., J. Allergy Clin. Immunol. in press). Natural birch pollen extract was prepared as described (Vrtala et al., Int. Arch. Allergy Immunol. 102 (1993) 160–169). Plasmid pET-17b containing the ampicillin resistance ansd a T7 promotor was obtained from Novagen, Madison, USA. Recombinant Bet v1 fragments were expressed in λDE3 lysogens of E. coli strain BL21 (F⁻ ompTr$_b$–m$_B$–) (Studier et al., Meth. Enzymol. 185 (1990) 60–89).

Expression of Bet v 1 (aa 1–74, aa 75–160) fragments in E. coli. Recombinant Bet v 1 fragments (aa 1–74, aa 75–160) were generated to maintain the epitopes (aa 40–65) of murine monoclonal antibodies which inhibited binding of allergic patients IgE to Bet v 1 (Lebecque et al., J. Allergy Clin. Immunol. in press) and in order to preserve major T-cell epitopes which had been mapped using overlapping peptides synthesized according to the Bet v 1 sequence (Ebner et al., J. Immunol. 150 (1993) 1047–1054). The cDNAs coding for fragment aa 1–74 and aa 75–160 were obtained by PCR amplification of the Bet v 1 cDNA using the following oligonucleotide primers (Pharmacia Biotech AB, Upsala Sweden):

```
Bet v 1 (aa 1-74):
   SEQ ID NO:9:
   5'GGG AAT TCC ATA TGG GTG TTT TCA ATT AC3'

SEQ ID NO:10:
   5'CGG GGT ACC TTA CTC ATC AAC TCT GTC CTT3'

Bet v 1 (aa 75-160):
   SEQ ID NO:11:
   5'GGG AAT TCC ATA TGG TGG ACC ACA CAA ACT3'

SEQ ID NO:12:
   5'CGG GGT ACC TTA GTT GTA GGC ATC GGA3'
```

The ECO R I sites which were incorporated in the first primers are underlined, Nde I and Kpn I sites are in italics.

To improve subcloning efficiency, PCR-products were first cut with Eco R I and Kpn I, purified by preparative agarose gel electrophoresis, subcloned into Eco R I and Kpn I site of plasmid pEt-17b (Novagen, Madison, USA) and transformed into E. coli BL21 (DE3) (Novagen, Madison, USA) by electroporation. Inserts were then excised with Nde I/Kpn I and subcloned again in plasmid pET-17b and transformed. Colonies expressing the correct fragments were identified by immunoscreening using mab 14 for Bet v 1 aa 1–74 and a rabbit anti-Bet v 1 C-terminal antiserum for Bet v1 aa 75-160. DNA from positive clones was isolated using Qiagen tips (Quiagen, Hilden, Germany) and both DNA strands were sequenced according to Sanger using a T7 polymerase sequencing kit (Pharmacia Biotech AB, Uppsala, Sweden) and $^{35}S$ dCTP (NEN, Stevehage, UK)(24). Recombinant Bet v 1 (aa 1–74 and Bet v1 (aa 75–160) were expressed in E. coli BL21 (DE3) by induction with 0.5 mM IPTG at an OD600 of 0.5–0.8 in liquid culture for 5 hours at 37° C.

Purification of recombinant Bet v1 (aa 1–74) and Bet V1 (aa 75–160). Bet v1 (aa 1–74) and Bet v1 (aa 75–160) were expressed in inclusion bodies isolated as described (Vrtala et al., J. Allergy Clin. Immunol. 97 (1996) 781–787). Inclusion bodies were solubilized with 8M urea, 10 mM Tris, pH 8, 1 mM EDTA (ethylenediaminetetraacetic acid), 5 mm β-mercaptoethanol, diluted with 10 mM Tris, pH 8 to a concentration of 6 M urea and centrifuged for 15 minutes at 10,000×g to remove insoluble material. The supernatant containing the recombinant protein, was dialyzed to a final concentration of 2M urea. Following centrifugation (15 min, 10,000×g), the supernatant was applied to a column packed with DEAE (diethylaminoethyl) Sepharose (Pharmacia Biotech AB) and the protein eluted with a 0–0.5M NaCl concentration gradient. Fractions, containing the recombinant protein which was more than 80% pure, were dialyzed against 6M urea, 10 mM NaH2PO4, pH 4.8 and rechromatographed on a column packed with SP Sepharose (Pharmacia Biotech AB). Fractions containing recombinant Bet v 1 (aa 1–74) or recombinant Bet v 1 (aa75–160) of greater than 95% purity, were dialyzed against 10 mM Tris, pH 7.5 and lyophilized until used.

IgE binding capacity of recombinant Bet v 1 and Bet v 1 fragments. Purified recombinant Bet v 1 and Bet v 1 fragments (aa 1–74, aa 75–160) were tested for IgE-binding capacity by Western blotting and in dot blot assays. For immunoblotting, approximately 1 μg/cm purified protein was separated by SDS-PAGE (Fling et al., Anal. Biochem. 155 (1986) 83–88) and blotted onto nitrocellulsoe according to Towbin (Towbin et al., Proc. Natl. Acad. Sci. USA 76 (1979) 4350–4353). To avoid denaturation of the proteins, dot blot experiments were performed in parallel. One μg of purified recombinant Bet v 1, 1 μg of each Bet v 1 fragment and 1 μg of bovine serum albumin and human serum albumin (HSA) (negative controls) were dotted on nitrocellulose strips.

Nitrocellulose strips containing Western blotted allergens or the dot blotted proteins were incubated with serum IgE from allergic individuals, non-allergic control individuals and buffer without addition of serum as described (Valenta et al., J. Exp. Med. 175 (1992) 377–385). Bound IgE antibodies were detected with $^{125}I$ labelled anti-human IgE antibodies and visualized by autoradiography.

Results: Sera of birch pollen allergic patients reacted with recombinant Bet v 1 but not with Bet v 1 fragments. Sera of grass pollen allergic individuals reacted neither with recombinant Bet v 1 nor with the recombinant Bet v 1 fragments.

Circular dichroism showed that the two Bet v 1 fragments showed no tendency to fold, even in the presence of each other.

Histamine release experiments. Granulocytes were isolated from heparinized blood of birch pollen allergic individuals by dextran sedimnetation (Valent et al., Proc. Natl. Acad. Sci. USA 86 (1989) 5542–5547). Cells were incubated with different concentrations (0.00 μg/ml-10 μg/ml) of purified recombinant Bet v 1, recombinant Bet v 1 fragments (aa 1–74, aa 75–160) separately and in equimolar mixture, or anti-human IgE antibodies. Histamine released in the supernatant was measured by radioimuoassay (RIA) (Immunotech, Marseille, France) (Valenta et al., J. Allergy Clin. Immunol. 91 (1993) 88–97). Total histamine was determined in cell lysates after freeze thawing. Results were obtained as mean values from triplicate determinations and expressed as percentage of total histamine release.

Results: Recombinant Bet v 1 fragments have approximately 1000 fold reduced capacity to induce histamine reslease from patients basophils compared to recombinant Bet v 1. An equimolar mixture of both Bet v 1 fragments did not induce significant release of histamine compared to each of the tested fragments.

Skin testing. Skin prick tests were performed on the individuals' forearms by placing μl of each solution (Pauli et al., J. Allergy Clin. Immunol. 97 (1996) 1100–1109; Menz et al., Clin. Exp. Allergy 26 (1996) 50–60). Recombinant Bet v 1 and recombinant Bet v 1 fragments were freshly dissolved in a 0.9% w/v sterile sodium chloride solution at concentrations of 100 μg/ml and 10 μg/ml. As controls birch pollen SQ (standard quality) extract, sodium chloride solution (negative control) and histamine hydrochloride (positive control)(ALK, Horsholm, Denmark) were used. Each drop was pricked with a fresh prick lancette (ALK, Horsholm, Denmark) and results were recorded after 20 minutes with a ball point pen by transferring the wheal area with a tape paper and by photography. The mean wheal diameter (Dm) was calculated by measuring the maximal longitudal diameter (D9 and the maximal transversal diiameter (d) according to the formula (D+d)/2=Dm.

Results: The two recombinant Bet v 1 fragments, neither alone nor in combination, do not elicit anaphylactic skin reactions compared to the intact recombinant Bet v 1.

TABLE 1

Proliferation of Bet v 1 specific T-cell clones with recombinant Bet v 1-polymers.

| 1 Epitop Bet v 1 | 2 TCC | 3 Control | 4 Bet v 1 | 5 Bet v 1-dimer | 6 Bet v 1-trimer | 7 Bet v 1-tetramer |
| --- | --- | --- | --- | --- | --- | --- |
| 1-15 | CGE 147 | 15567 | 47570 | 97939 | 67299 | 79741 |
| 1-18 | HC 26/II | 1264 | 9977 | 32667 | 14170 | 22178 |
| 10-27 | WF 110/III | 87 | 6402 | 12571 | 5823 | 9542 |
| 10-27 | WF 110/III | 146 | 3575 | 13340 | 5428 | 6961 |
| 10-27 | WF 121/III | 287 | 3914 | 22099 | 5117 | 13000 |
| 11-27 | TF 7B | 359 | 10492 | 42352 | 9869 | 29900 |
| 35-48 | HC 3/III | 40.7 | 10499 | 21301 | 15761 | 25609 |
| 64-75 | CGE 110 | 612 | 107103 | 121178 | 96135 | 117930 |
| 64-75 | CGE 31 | 2937 | 71176 | 55728 | 38955 | 67625 |
| 64-75 | CGE 33 | 3096 | 99633 | 85438 | 80077 | 91755 |
| 77-93 | WF 29R | 143 | 12638 | 28579 | 14576 | 14677 |
| 77-93 | GZ 17M | 172 | 61463 | 90586 | 54988 | 84237 |
| 88-10 | CGE 34 | 515 | 16045 | 20531 | 14176 | 15217 |
| 93-110 | TF 1M | 438 | 21423 | 29741 | 11500 | 23454 |
| 106-120 | WF 9/III | 305 | 43203 | 81605 | 32735 | 65592 |
| 109-120 | WD 7/III | 130 | 53362 | 41875 | 50489 | 48601 |
| 110-128 | HC 33/II | 134 | 18099 | 46022 | 17917 | 42051 |
| 112-123 | WF 112/III | 85 | 10494 | 12778 | 7585 | 11106 |
| 112-123 | WF 97/III | 91 | 4569 | 6884 | 3352 | 5950 |
| 127-138 | GZ 10A | 182 | 3347 | 8379 | 3227 | 6645 |
| 141-156 | TF 10A | 215 | 4862 | 4438 | 2232 | 57 |
| 141-156 | RR4R | 1416 | 88361 | 85594 | 102303 | 117122 |
| 141-156 | SAZ 10/IV | 612 | 5121 | 3830 | 5207 | 3979 |

TABLE 2

Skin testing with recombinant Bet v 1-monomer and polymers

| Individual | Histamine | birch | Bet v 1 monomer 10 μg/ml | Bet v 1 monomer 100 μg/ml | Bet v 1 dimer 10 μg/ml | Bet v 1 dimer 100 μg/ml | Bet v 1 trimer 10 μg/ml | Bet v 1 trimer 100 μg/ml |
| --- | --- | --- | --- | --- | --- | --- | --- | --- |
| birch pollen allergic patients | | | | | | | | |
| MS | 8 | 5.5 | 4 | 7 | 3 | 6 | 0 | 0 |
| SF | 6 | 7 | 8 | 12 | 7.5 | 8 | 2 | 5.5 |
| PSt | 8 | 7 | 6.5 | 16 | 6 | 7 | 2 | 4.5 |
| SO | 6.5 | 5.5 | 5.5 | 14 | 0 | 4.5 | 0 | 3.5 |
| SS | 4.5 | 8 | 5.5 | 9 | 0 | 4 | 0 | 0 |

TABLE 2-continued

Skin testing with recombinant Bet v 1-monomer and polymers

| Individual | Histamine | birch | Bet v 1 monomer 10 µg/ml | Bet v 1 monomer 100 µg/ml | Bet v 1 dimer 10 µg/ml | Bet v 1 dimer 100 µg/ml | Bet v 1 trimer 10 µg/ml | Bet v 1 trimer 100 µg/ml |
|---|---|---|---|---|---|---|---|---|
| MD | 5.5 | 9.5 | 7 | 11.5 | 4.5 | 7 | 0 | 5 |
| non-allergic controls | | | | | | | | |
| TB | 6 | 0 | 0 | 0 | 0 | 0 | 0 | 0 |
| VR | 8.5 | 0 | 0 | 0 | 0 | 0 | 0 | 0 |
| CD | 6.5 | 0 | 0 | 0 | 0 | 0 | 0 | 0 |
| TL | 9 | 0 | 0 | 0 | 0 | 0 | 0 | 0 |

| patient # | | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|---|
| Inhibition of IgE binding In % | moAb A | 49 | — | — | 57 | 93 | 96 | — | 41 | — | 41 | 27 | — | 29 | 47 | — |
| | moAb B | 96 | — | — | 45 | — | 97 | — | 31 | — | 45 | 24 | — | — | 26 | — |

| patient # | | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|
| Inhibition of IgE binding in % | moAb A | 19 | 21 | 35 | — | 36 | — | — | 10 | 20 | 51 | 30 | — | 30 | — | 55 |
| | moAb B | 24 | 25 | 12 | 14 | 21 | — | — | — | 22 | 31 | 33 | — | 24 | — | 50 |

| patient # | | 31 | 32 | 33 | 34 | 35 | 36 | 37 | 38 | 39 | 40 | 41 | 42 | 43 | 44 | 45 |
|---|---|---|---|---|---|---|---|---|---|---|---|---|---|---|---|---|
| Inhibition of IgE binding In % | moAb A | 10 | 28 | 6 | 18 | 23 | 23 | 3 | — | 46 | 22 | — | 8 | 30 | 80 | 33 |
| | moAb B | 4 | 90 | 5 | 59 | 87 | 97 | 13 | — | 18 | 19 | 65 | 80 | 10 | 94 | 17 |

| patient # | | 46 | 47 | 48 | 49 | 50 | 51 | 52 | 53 | 54 | 55 | 56 | 57 | 58 | 59 | 60 |
|---|---|---|---|---|---|---|---|---|---|---|---|---|---|---|---|---|
| Inhibition of IgE binding in % | moAb A | — | 6 | 54 | 30 | 36 | 12 | — | — | — | 72 | 31 | 1 | 12 | 38 | — |
| | moAb B | — | 31 | 97 | — | 35 | 6 | — | — | — | 67 | 41 | — | 10 | 28 | — |

The invention claimed is:

1. An immunogen derived from Bet v 1 protein allergen, comprising
   a) a non-anaphylactic immunogenic recombinant fragment of the protein allergen, said fragment comprising an IgG epitope and an IgE epitope of the protein allergen partly but not completely overlapping;
   b) a polymeric form of said fragment, in which form the fragment constitutes the monomeric units, wherein said monomeric units are separated from each other by an oligopeptide linker; or
   c) a non-anaphylactic recombinant polymeric form of said protein allergen consisting of 2 to 10 monomeric units in which the protein allergen constitutes the monomeric units, wherein said monomeric units are separated from each other by an oligopeptide linker.

2. The immunogen of claim 1, wherein said immunogen is according to (b) or (c) and said oligopeptide linker comprises 1–30 amino acid residues.

3. The immunogen of claim 2, wherein said amino acid residues are hydrophilic.

4. An immunogen derived from Bet v 1 protein allergen, comprising a non-anaphylactic immunogenic recombinant fragment of the protein allergen, said fragment comprising an IgG epitope and an IgE epitope of the protein allergen partly but not completely overlapping, wherein the fragment comprises SEQ ID NO: 19.

5. An immunogen derived from Bet v 1 protein allergen, comprising a non-anaphylactic immunogenic recombinant fragment of the protein allergen, said fragment comprising an IgG epitope and an IgE epitope of the protein allergen partly but not completely overlapping, wherein the fragment comprises SEQ ID NO:20.

6. An immunogen derived from Bet v 1 protein allergen, comprising a non-anaphylactic immunogenic recombinant fragment of the protein allergen, said fragment comprising an IgG epitope and an IgE epitope of the protein allergen partly but not completely overlapping, wherein the fragment comprises SEQ ID NO:21.

7. The immunogen of claim 1, comprising a non-anaphylactic immunogenic recombinant fragment of the protein allergen, said fragment comprising an IgG epitope and an IgE epitope of the protein allergen partly but not completely overlapping.

8. An immunogen derived from Bet v 1 protein allergen, comprising
   a polymeric form of a non-anaphylactic immunogenic recombinant fragment of the protein allergen, said fragment comprising an IgG epitope and an IgE epitope of the protein allergen partly but not completely overlapping, in which form the fragment constitutes the monomeric units, wherein said monomeric units are separated from each other by an oligopeptide linker and
   wherein the polymeric form of said fragment is recombinantly produced.

* * * * *

SEQUENCE LISTING

<160> NUMBER OF SEQ ID NOS: 21

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 1
gaggaattcc atatgggtgt tttcaattac                              30

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 2
cggggtacca agttgtaggc atcggagtg                               29

```
<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 3
cggggtaccg atgggtgttt tcaattac                                    28

<210> SEQ ID NO 4
<211> LENGTH: 42
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 4
ccggaattcc cgctcgagct attagttgta ggcatcggag tg                    42

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 5
cggggtgatg ggtgttttca attac                                       25

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 6
cggaattcac tagtgggttg taggcatcgg agtg                             34

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 7
ccggaattcg gactagtaat gggtgttttc aattac                           36

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 8
cggaattcgt tgtaggcatc ggagtg                                      26

<210> SEQ ID NO 9
```

```
<211> LENGTH: 29
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 9
gggaattcca tatgggtgtt ttcaattac                                29

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 10
cggggtacct tactcatcaa ctctgtcctt                               30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 11
gggaattcca tatggtggac cacacaaatc                               30

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide Primer

<400> SEQUENCE: 12
cggggtacct tagttgtagg catcgga                                  27

<210> SEQ ID NO 13
<211> LENGTH: 24
<212> TYPE: DNA
<213> ORGANISM: Betula sp.
<220> FEATURE:
<221> NAME/KEY: CDS
<222> LOCATION: (1)..(24)

<400> SEQUENCE: 13 atg aac ttg gta ccg atg aac taa                               24
Met Asn Leu Val Pro Met Asn
  1               5

<210> SEQ ID NO 14
<211> LENGTH: 7
<212> TYPE: PRT
<213> ORGANISM: Betula sp.

<400> SEQUENCE: 14

Met Asn Leu Val Pro Met Asn
  1               5

<210> SEQ ID NO 15
<211> LENGTH: 144
```

```
<212> TYPE: DNA
<213> ORGANISM: Betula sp.
<220> FEATURE:
<221> NAME/KEY: CDS
<222> LOCATION: (1)..(144)

<400> SEQUENCE: 15 atg aac ttg gta ccg atg aac cca cta gta atg aac gaa ttc tgc aga      48
Met Asn Leu Val Pro Met Asn Pro Leu Val Met Asn Glu Phe Cys Arg
  1               5                  10                  15 tat cca tca cac tgg cgg ccg ctc gag cag atc cgg ctg cta aca aag      96
Tyr Pro Ser His Trp Arg Pro Leu Glu Gln Ile Arg Leu Leu Thr Lys
             20                  25                  30 ccc gaa agg aag ctg agt tgg ctg ctg cca ccg ctg agc aat aac tag     144
Pro Glu Arg Lys Leu Ser Trp Leu Leu Pro Pro Leu Ser Asn Asn
         35                  40                  45

<210> SEQ ID NO 16
<211> LENGTH: 47
<212> TYPE: PRT
<213> ORGANISM: Betula sp.

<400> SEQUENCE: 16

Met Asn Leu Val Pro Met Asn Pro Leu Val Met Asn Gly Phe Cys Arg
  1               5                  10                  15

Tyr Pro Ser His Trp Arg Pro Leu Glu Gln Ile Arg Leu Leu Thr Lys
             20                  25                  30

Pro Glu Arg Arg Leu Ser Trp Leu Leu Pro Pro Leu Ser Asn Asn
         35                  40                  45

<210> SEQ ID NO 17
<211> LENGTH: 51
<212> TYPE: DNA
<213> ORGANISM: Betula sp.
<220> FEATURE:
<221> NAME/KEY: CDS
<222> LOCATION: (1)..(51)

<400> SEQUENCE: 17 atg aac ttg gta ccg atg aac cca cta gta atg aac gaa ttc atg aac      48
Met Asn Leu Val Pro Met Asn Pro Leu Val Met Asn Glu Phe Met Asn
  1               5                  10                  15 taa                                                                  51

<210> SEQ ID NO 18
<211> LENGTH: 16
<212> TYPE: PRT
<213> ORGANISM: Betula sp.

<400> SEQUENCE: 18

Met Asn Leu Val Pro Met Asn Pro Leu Val Met Asn Glu Phe Met Asn
  1               5                  10                  15

<210> SEQ ID NO 19
<211> LENGTH: 12
<212> TYPE: PRT
<213> ORGANISM: Betula sp.

<400> SEQUENCE: 19

Gly Pro Gly Thr Ile Lys Lys Ile Ser Phe Pro Glu
  1               5                  10

<210> SEQ ID NO 20
<211> LENGTH: 12
```

```
<212> TYPE: PRT
<213> ORGANISM: Betula sp.

<400> SEQUENCE: 20

Thr Ile Lys Lys Ile Ser Phe Pro Glu Gly Phe Pro
 1               5                   10

<210> SEQ ID NO 21
<211> LENGTH: 12
<212> TYPE: PRT
<213> ORGANISM: Betula sp.

<400> SEQUENCE: 21

Lys Ile Ser Phe Pro Glu Gly Phe Pro Phe Lys Tyr
 1               5                   10
```